United States Patent
Osbrach

(10) Patent No.: US 10,407,889 B1
(45) Date of Patent: Sep. 10, 2019

(54) TOILET WASH

(71) Applicant: Allen Z. Osbrach, Merritt Island, FL (US)

(72) Inventor: Allen Z. Osbrach, Merritt Island, FL (US)

(*) Notice: Subject to any disclaimer, the term of this patent is extended or adjusted under 35 U.S.C. 154(b) by 0 days.

(21) Appl. No.: 15/965,294

(22) Filed: Apr. 27, 2018

(51) Int. Cl.
| | |
|---|---|
| *E03D 9/08* | (2006.01) |
| *A47K 3/26* | (2006.01) |
| *A61M 3/02* | (2006.01) |
| *A47K 7/08* | (2006.01) |

(52) U.S. Cl.
CPC ............ *E03D 9/085* (2013.01); *A47K 3/26* (2013.01); *A47K 7/08* (2013.01); *A61M 3/025* (2013.01)

(58) Field of Classification Search
CPC ............ A47K 3/26; A47K 7/08; A47K 3/025
USPC ............................................. 4/420.1–420.5
See application file for complete search history.

(56) References Cited

U.S. PATENT DOCUMENTS

| | | | |
|---|---|---|---|
| 2,691,373 A | 10/1954 | Bried | |
| 4,287,618 A | 9/1981 | Silver | |
| 4,441,219 A | 4/1984 | Epstein | |
| 4,903,347 A | 2/1990 | Garcia et al. | |
| 4,995,121 A | 2/1991 | Barker | |
| 5,419,363 A * | 5/1995 | Robinson | E03C 1/021 137/360 |
| 5,937,451 A | 8/1999 | Mihara | |
| 6,209,800 B1 | 4/2001 | Thomas | |
| 6,973,679 B1 * | 12/2005 | Schad | E03D 9/085 4/420.4 |
| 7,127,750 B2 | 10/2006 | Lim | |
| 2005/0229300 A1 * | 10/2005 | Wilcox | E03D 9/085 4/420.4 |
| 2007/0209102 A1 * | 9/2007 | Lim | A47K 4/00 4/420.4 |
| 2008/0092283 A1 * | 4/2008 | Cruz | E03D 9/085 4/420.4 |
| 2008/0116226 A1 * | 5/2008 | Py | B65D 75/5866 222/207 |
| 2008/0216226 A1 | 9/2008 | Hamlin | |

(Continued)

OTHER PUBLICATIONS

Cleanstream Toilet Enema Attachment Set: Health & Personal Care, retrieved from http://www.amazon.com/Cleanstream-Toilet-Enema-Attachment-Set/dp/B01HQWYJQ0, retrieved on Apr. 26, 2018, 6 pages.

(Continued)

*Primary Examiner* — Huyen D Le
(74) *Attorney, Agent, or Firm* — Brian S. Steinberger; Law Offices of Brian S. Steinberger, P.A.

(57) ABSTRACT

Systems, devices, and methods for providing a spray wand with a disposable wand head tube that can be attached to a toilet water supply that can be used with toilet paper to remove fecal matter material and urine that wiping was not able to remove. A dual shot off valve can be attached to an inlet water line from a wall adjacent to the toilet. A first supply line can pass from one of the valves to the toilet and a second supply line can be attached to the other one of the dual valves, and an opposite end attached to a single valve for the supplying water to the disposable wand head tube. The disposable wand head tube can be formed from a paper straw and a plastic tube, and the like. The disposable wand tubes can have bent end portions and come in packs.

20 Claims, 3 Drawing Sheets

(56) References Cited

U.S. PATENT DOCUMENTS

2011/0302709 A1* 12/2011 Taylor ................. A47K 7/08
4/443

OTHER PUBLICATIONS

Cleanstream Silicone Comfort Nozzle Enema Attachment, retrieved from http://www.amazon.com/Cleanstream-Silicone-Comfort-Nozzle-Attachment/dp/B00767N, retrieved on Apr. 26, 2018, 6 pages.
Toilet Enema Attachment Set, EnemaSupply, retrieved from https://enemasupply.com/products/toilet-enema-attachment?variant=35314199250&gclid=, retrieved on Apr. 26, 2018, 2 pages.
GoBidet Hand Held Bidet in White, retrieved from https://www.homedepot.com/p/GoBidet-Hand-Held-Bidet-in-White-2012W/204622705, retrieved on Apr. 26, 2018, 2 pages.

\* cited by examiner

TOILET WASH

FIELD OF INVENTION

This invention relates to improving personal hygiene to maintain health and prevent the spread of diseases, and in particular to systems, devices, and methods for providing a spray wand with a disposable wand head that can be attached to a toilet water supply that can be used with toilet paper to remove fecal matter material and urine that wiping was not able to remove.

BACKGROUND AND PRIOR ART

The popular use of toilet paper after a bowel movement does not remove all the human's waste from a person's body. In fact, the action of wiping with toilet paper actually spreads waste over the area that was wiped leaving an unpleasant odor and potentially causing other health issues. This should not be glossed over because common sense dictates leaving surface waste material on your body can only be hazardous.

Just using more toilet paper does not fix the problem since excessive amounts of toilet paper can cause uncomfortable skin abrasions. Excessive use of toilet paper is also a waste of paper which can become expensive over time. In addition, excessive amounts of toilet paper can cause a toilet to become clogged and need to be separately cleaned.

Thus, the need exists for solutions to the above problems with the prior art.

SUMMARY OF THE INVENTION

A primary objective of the present invention is to provide systems, devices, and methods for providing a spray wand with a disposable wand head that can be attached to a toilet water supply, that can be used in combination with toilet paper to remove fecal matter material and urine that wiping was not able to remove.

A secondary objective of the present invention is to provide systems, devices, and methods for providing a spray wand with a disposable wand head, for use with toilet paper to remove fecal matter material and urine that wiping was not able to remove, which is less expensive than using extra amounts of toilet paper as a cleaning wipe.

A third objective of the present invention is to provide systems, devices, and methods for providing a spray wand with a disposable wand head, for use with toilet paper to remove fecal matter material and urine that wiping was not able to remove, which reduces the chances of clogging the toilet not just using toilet paper as a cleaning source.

A fourth objective of the present invention is to provide systems, devices, and methods for providing a spray wand with a disposable wand head, for use with toilet paper to remove fecal matter material and urine that wiping was not able to remove, which is less harmful to the skin than using extra toilet paper as the sole wipe source.

A fifth objective of the present invention is to provide systems, devices, and methods for providing a spray wand with a disposable wand head, for use with toilet paper to remove fecal matter material and urine that is efficient and will leave the body clean.

For proper hygiene, it is well known that we do not accept just wiping our hands before eating; we thoroughly wash our hands to prevent contamination, then we dry our hands with paper towels.

The subject invention takes the hand washing and wiping concept and applies it what a user should be This is similar to what we should be doing after using the bathroom.

Further objects and advantages of this invention will be apparent from the following detailed description of the presently preferred embodiments which are illustrated schematically in the accompanying drawings.

BRIEF DESCRIPTION OF THE FIGURES

The drawing figures depict one or more implementations in accord with the present concepts, by way of example only, not by way of limitations. In the figures, like reference numerals refer to the same or similar elements.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

Figure 1:
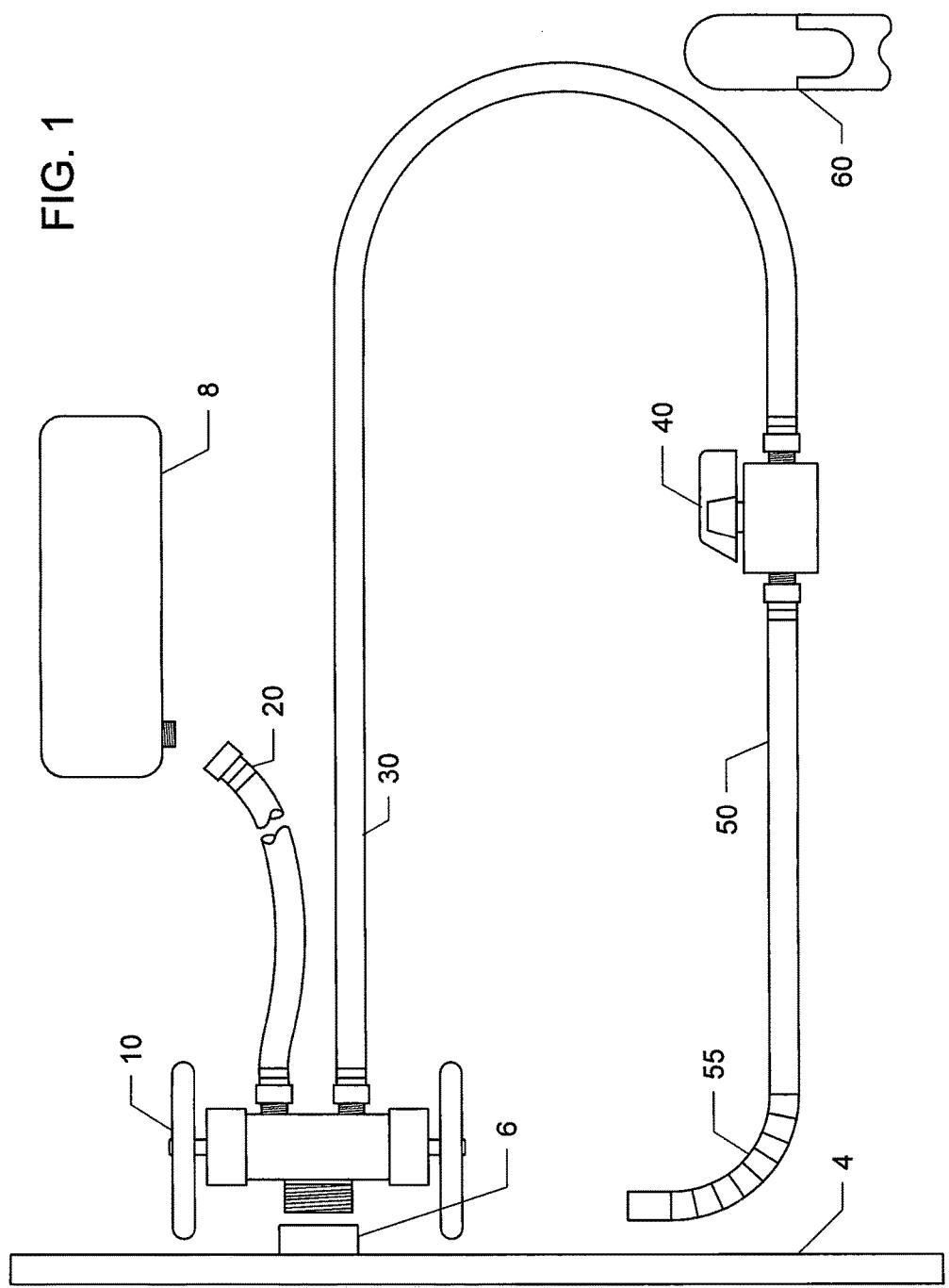
FIG. 1 is an exploded view of the toilet wash cleaning system.
Figure 2:
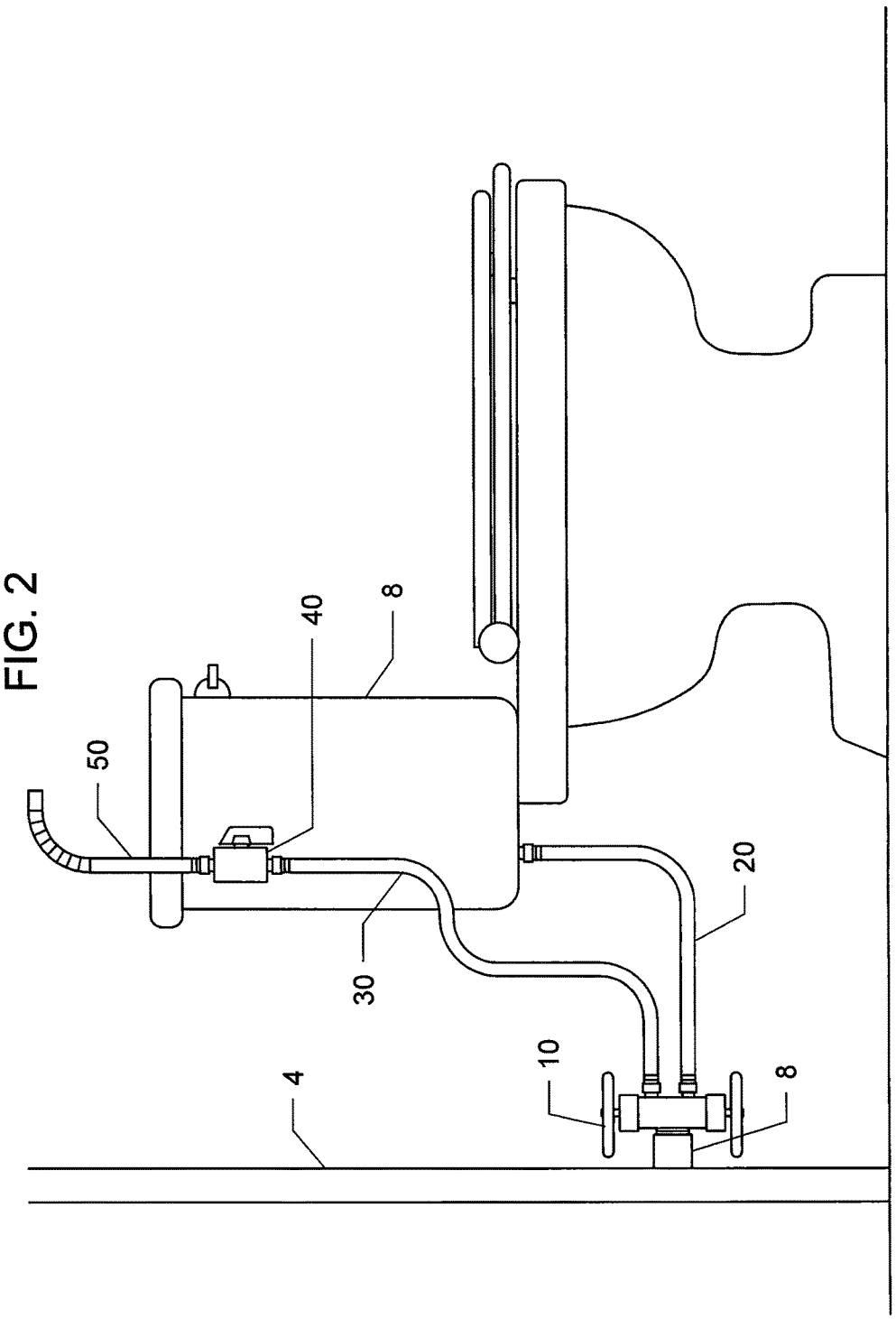
FIG. 2 is another view of the toilet wash system of FIG. assembled together and attached to a toilet ready for use.

A list of components will now be described.
1 Toilet wash system
4 wall
6 water supply line inlet in wall
8 toilet (water closet)
10 dual outlet shut off valve with two valves
20 supply line to water closet
30 supply line for wash system
40 main single valve for the disposable tube
50 disposable tube
55 fixed bent section of tube/bendable parallel rings
70 barb connector
75 barbs FIG. 1 is an exploded view of the toilet wash cleaning system 1. FIG. 2 is another view of the toilet wash system 1 of FIG. 1 assembled together and attached to a toilet 8 ready for use.

Referring to FIGS. 1-2, the toilet wash system can include dual outlet shut off valve 10 having an inlet port that can be attached to the water supply line outlet 6 that is usually located on a wall 4 of a bathroom. The dual outlet shut off valve 10 can have two rotatable knobs that each control water outflow from the dual valve 10. A first outlet from the valve 10 can pass through an approximately ⅜" supply line to a water closet (toilet) 8.

The second outlet from the dual valve 10 can control water supply to an elongated supply line 30, that can have two approximately ¼" fittings on both ends. The outer end of the supply line 30 can be attached to a main valve 40 having a rotatable lever, such as but not limited to an approximately ¼" mini brass valve (female×female NPT). Main valve 40 can have an outlet port that allows for a base of a disposable tube 50 to be attached thereto. The disposable tube 50 can have at least one bend 55 for allowing the outer end to be used as wand to direct water flow to a desired area. The disposable tube 50 can have a cylindrical outlet tip. Optionally, the outlet tip can be oval opening to better direct a water spray.

Referring to FIGS. 1-2, when a person is ready to wipe themselves after using the toilet 8, they can wipe themselves in the traditional way and then use the toilet wash system 1 by spraying water from the disposable tube 50 on to the external areas that came in contact with surface waste material. To remove additional residue that toilet paper could not. Or simply skip wiping themselves and rinse them self off with the toilet wash system 1.

The toilet wash system 1 will remove but not limited to fecal material, urine and menstrual discharge materials (here after referred to as surface waste material) that stayed on the surface of your body that wiping was not able to completely remove. After washing with the toilet wash system, toilet paper can be used to dry those areas.

The toilet wash system rinses off a person's private areas with a disposable toilet tube 50 so the possibility of spreading bacteria, viruses or fungi to the next person that uses the toilet 8 is greatly reduced.

The toilet wash system 1 can improve our health habits by removing the surface waste materials left on the person after using the bathroom. The toilet wash system 1 does that by washing off any surface waste materials by using a stream of water through the disposable toilet tube 50 to wash off any residue of waste remaining on the person's body. This reduces the possibility of that person spreading disease when coming in contact with another person. Because the disposable tube 50 is disposable after one use, the possibility of contamination from the surface waste material is eliminated. The disposable tube 50 is then disposed of after a single use, similar to the disposal of toilet paper.

The disposable tube 50 that is cellulose (paper) is biodegradable and can simply be flushed down the toilet. A preferred embodiment of the paper straw includes a length of approximately 7¾", an outside diameter of approximately 15/64", and an inside diameter of approximately 3/16".

The cellulose (paper) tubes can resemble straws and include a plurality of rings 55 along their length and preferably the rings located between a mid-portion of the tube and the outlet end of the tube. The plurality of rings 55 (FIG. 3) allow for the tube to be easily bendable from a straight position to bend up to approximately 90 degrees or more.

Figure 3:
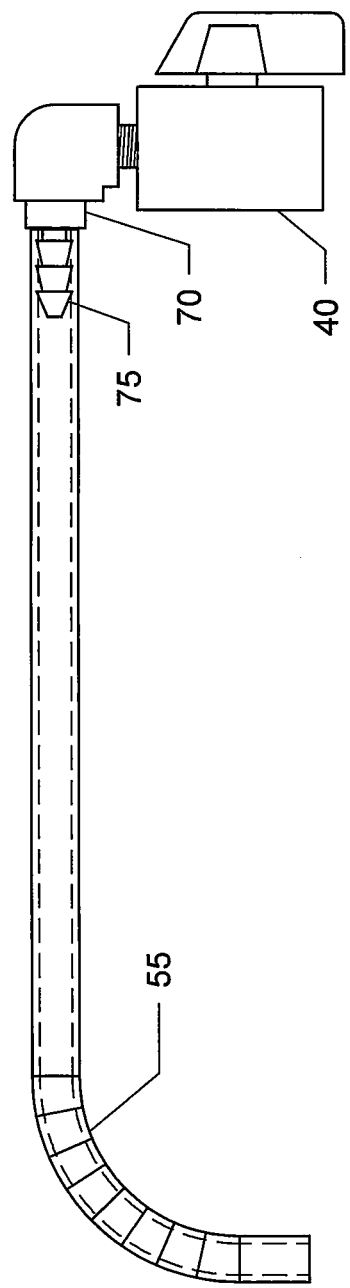
FIG. 3 is an enlarged cross-sectional view of the hose barb adapters which provide a friction fit to attach the disposable tubes to the main valve.

The disposable paper (cellulose) straw 50 can be sized to fit an approximately 3/16" hose barb as shown in FIG. 3.

The plastic tubes 50 should always be thrown away after every use. The disposable tube's 50 unique design to be replaced after a single use, will ensures that disease will not be spread to the next person.

A first preferred embodiment of the disposable plastic straw can include a length of approximately 10¼", an outside diameter of approximately 7/32", and an inside diameter of approximately 3/16".

The disposable plastic straw 50 can be sized to fit an approximately 5/16" hose barb (as shown in FIG. 3).

A second preferred embodiment of the disposable plastic straw can include a length of approximately 10½", an outside diameter of approximately 11/32", and an inside diameter of approximately 5/16".

A third preferred embodiment of the disposable plastic straw can include a length of approximately 11⅞", an outside diameter of approximately 11/32", and an inside diameter of approximately 5/16".

A fourth preferred embodiment of the disposable silicone straw can include a length of approximately 10 & ⅜", an outside diameter of approximately 0.45", and an inside diameter of approximately 0.35".

The toilet wash system 1 can start with a dual outlet shut-Off valve 10 which would replace the existing single toilet valve. Once the existing toilet valve is removed and replaced with the dual outlet shut-off valve 10, the approximately ⅜" supply of the dual outlet shut-off valve 10 will be reattached to the toilet 8. Water from the approximately ¼" side of the dual outlet shut-off valve 10 can be used to supply water for the toilet wash system 1.

A water supply line 20 can be attached on one end to the dual outlet shut-off valve 20 and the other end can be attached to an adapter compression inch OD×inch MIP(C) for the purpose of connecting it to the approximately ¼ inch mini brass ball valve 40. The mini brass ball valve 40 can achieve the desired amount of water flow of water.

Referring to FIGS. 1-3, on the other side of the mini brass ball valve 40 can include a hose barb adapter connector 70 having barbs 75 that can come in three sizes approximately 3/16" or approximately 5/16" or approximately ⅜"×approximately ¼" MIP.

The Hose Barb Adapter connectors 70 can allow the user to use different size disposable toilet tubes 50. The user can simply slide the disposable toilet tubes 50 on the hose barb adapter connector 70 and turn on the water by rotating lever on main valve 40. The disposable toilet tube 50 simply slides on and off with no clamps or fasteners it simply uses friction.

The inherent design of a hose barb adapter connector 70 is to slide the disposable toilet tube 50 over the hose barb adapter connector 70 where its leak free. This creates a quick and effortlessly way to clean yourself with the flow of water that will remove materials that toilet paper can't remove.

Three different hose barb adapter connectors 70 can be used, which include a straight hose barb adapter connector, an approximately 45° hose barb adapter connector and an approximately 90° hose barb adapter connector. The approximately 90 degree hose barb adapter connector would work best.

The disposable toilet tube can come in different materials paper (cellulose) and plastic. The paper disposable toilet tube 50 is the most environmentally friendly and can be flushed down the toilet which makes it similar to toilet paper in that respect. It can come in round or oval shapes. The oval shape can start approximately 1" from the end of the disposable toilet tube 50. It can be preferred because it is more, narrow making it easier to get closer to the surface waste materials.

The plastic disposable toilet tube 50 can be the least inexpensive. All disposable toilet tubes 50 should be thrown away after every use and should not ever be used internally. The water passing through the disposable toilet tube 50 can clean the external body parts such as but not limited to: penis, anus and vagina here after referred to as private areas.

The disposable tube 50 can be held by the person sitting on the toilet 8. The person can use the water coming out of the water to wash off the private areas. After using the disposable toilet tube 50 it should be thrown away to ensure that there is no possibility of transferring of germs to the next person. A new disposable toilet tube 50 should be installed to ensure that there is no possibility to spread any type of germs or parasites.

After a new disposable tube 50 is installed, the single mini ball valve 40 can then be placed in the valve holder 60, that can be mounted to a side of the toilet 8, or the side of a wall, and the like.

The toilet wash system 1 is a unique way to keep bacteria, viruses, parasites, and fungus off of private areas of humans.

The term "approximately" can be +/−10% of the amount referenced. Additionally, preferred amounts and ranges can include the amounts and ranges referenced without the prefix of being approximately.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A toilet wash system, comprising:
    a dual outlet shut off valve having an inlet for being attached to a toilet water supply, and having a first outlet with a first shut off valve turn knob and a second outlet with a second shut off valve turn knob;
    a first supply line attached to the first outlet and an opposite end for being attached to a water inlet port of a toilet;
    a second supply line attached to the second outlet and an outlet end;
    a single valve with an inlet port attached to the outlet end of the second supply line, and an outlet; and
    a disposable elongated cleaning tube having an inlet end attached to the outlet of the single valve, and an outlet end, wherein users turn water on to the cleaning tube by rotating the second shut off valve turn knob and the single valve so that water passes out the outlet port of the disposable elongated cleaning tube, and wherein the cleaning tube is used to flush waste away.

2. The toilet wash system of claim 1, further comprising:
    a holder hook for mounting the disposable toilet tube adjacent on a side of the toilet.

3. The toilet wash system of claim 1, wherein the single valve includes: an approximately ¼" mini brass valve with female×female NPT.

4. The toilet wash system of claim 1, wherein the disposable elongated cleaning tube includes:
    a disposable paper straw.

5. The toilet wash system of claim 4, wherein the paper straw includes a length of approximately 7¾", an outside diameter of approximately 15/64", and an inside diameter of approximately 3/16".

6. The toilet wash system of claim 1, wherein the disposable elongated cleaning tube includes:
    a disposable plastic straw.

7. The toilet wash system of claim 6, wherein the disposable plastic straw includes a length of approximately 10¼", an outside diameter of approximately 7/32", and an inside diameter of approximately 3/16".

8. The toilet wash system of claim 6, wherein the disposable plastic straw includes a length of approximately 9½", an outside diameter of approximately 11/32", and an inside diameter of approximately 5/16".

9. The toilet wash system of claim 6, wherein the disposable plastic straw includes a length of approximately 11⅞", an outside diameter of approximately 11/32", and an inside diameter of approximately 5/16".

10. The toilet wash system of claim 1, wherein the disposable elongated cleaning tube includes:
    a disposable silicone straw.

11. The toilet wash system of claim 1, wherein the disposable elongated cleaning tube includes:
    a plurality of parallel rings between the inlet end and the outlet end of the tube, the plurality of parallel rings allowing the outlet end of the tube to be selectively bent from a straight position to an approximately 90 degree bend.

12. The toilet wash system of claim 1, wherein the disposable elongated cleaning tube includes:
    a fixed bent angle between a mid-portion of the tube and the outlet end of the tube.

13. The toilet wash system of claim 12, wherein the fixed bent angle is between approximately 20 degrees and approximately 90 degrees.

14. The toilet wash system of claim 13, wherein the fixed bent angle is approximately 45 degrees.

15. The toilet wash system of claim 1, further comprising:
    a barb connector having one end attached to the main valve and an opposite end having a plurality of barbs that are press fit into the inlet end of the disposable tube.

16. The toilet wash system of claim 15, wherein the barb connector includes an approximately 3/16" hose barb.

17. The toilet wash system of claim 16, wherein the disposable tube includes a paper tube having an inlet end that fits over the approximately 3/16" hose barb.

18. The toilet wash system of claim 1, wherein the disposable elongated cleaning tube includes:
    a package of a plurality of identical disposable elongated cleaning tubes.

19. A toilet wash kit, comprising:
    a dual outlet shut off valve having an inlet for being attached to a toilet water supply, and having a first outlet with a first shut off valve turn knob and a second outlet with a second shut off valve turn knob;
    a first supply line attached to the first outlet and an opposite end for being attached to a toilet;
    a second supply line attached to the second outlet and having an outlet end;
    a single valve attached to the outlet end of the second supply line, and an outlet port; and
    a disposable elongated cleaning tube having an inlet end attached to the outlet port of the single valve, and an outlet end, wherein users turn water on to the cleaning tube by rotating both the second shut off valve turn knob and the single lever valve so that water can pass out of the outlet port of the disposable elongated cleaning tube, wherein the cleaning tube is used to flush waste away.

20. The toilet wash kit of claim 19, further comprising:
a barb connector having one end attached to the single valve and an opposite end having a plurality of barbs that are press fit into the inlet end of the disposable tube, wherein the disposable tube includes a paper tube having a plurality of rings along a portion of the disposable tube.

* * * * *